United States Patent
Novak et al.

[11] Patent Number: 5,921,953
[45] Date of Patent: Jul. 13, 1999

[54] DEVICE FOR THE RINSING OF BODY CAVITIES

[75] Inventors: Paul Novak, Schaffhausen, Switzerland; Jacques Hamou, Paris; Arnaud Wattiez, Clermont-Ferrand, both of France

[73] Assignee: Storz Endoskop GmbH, Switzerland

[21] Appl. No.: 09/068,756

[22] PCT Filed: Nov. 8, 1996

[86] PCT No.: PCT/DE96/02138

§ 371 Date: Jul. 9, 1998

§ 102(e) Date: Jul. 9, 1998

[87] PCT Pub. No.: WO97/17093

PCT Pub. Date: May 15, 1997

[30] Foreign Application Priority Data

Nov. 8, 1995 [DE] Germany .......................... 195 41 633

[51] Int. Cl.⁶ .................................................. A61M 1/00
[52] U.S. Cl. ...................................... 604/31; 128/DIG. 13
[58] Field of Search .................................. 604/31, 27, 35, 604/43, 19; 128/DIG. 13, DIG. 12

[56] References Cited

U.S. PATENT DOCUMENTS

| | | |
|---|---|---|
| 4,261,360 | 4/1981 | Perez . |
| 4,600,401 | 7/1986 | Kamen ............................ 128/DIG. 13 |
| 5,178,606 | 1/1993 | Ognier et al. . |
| 5,356,378 | 10/1994 | Doan ................................ 128/DIG. 13 |
| 5,423,747 | 6/1995 | Amano ...................................... 604/31 |
| 5,470,312 | 11/1995 | Zanger et al. .................... 128/DIG. 13 |
| 5,503,626 | 4/1996 | Goldrath ................................... 604/31 |
| 5,556,378 | 9/1996 | Storz et al. ............................... 604/31 |
| 5,662,611 | 9/1997 | Bieiser et al. ................... 128/DIG. 13 |
| 5,810,765 | 9/1998 | Oda .......................................... 604/31 |
| 5,830,180 | 11/1995 | Chandler et al. ......................... 604/35 |

FOREIGN PATENT DOCUMENTS 44 17 189 A1  11/1995  Germany .
WO 93/22979  11/1993  WIPO .

OTHER PUBLICATIONS

Olympus Winter & Ibe GmbH, "Instruction manual: Uteromat fluid control A4060," 1995, pp. 2–53.

*Primary Examiner*—Paul J. Hirsch
*Attorney, Agent, or Firm*—St.Onge Steward Johnston & Reens

[57] ABSTRACT

The invention relates to an apparatus for irrigating body cavities with a fluid, comprising a reservoir containing the irrigating fluid, a pumping unit which pumps the irrigating fluid from the reservoir via an instrument into the body cavity to be treated, a collector vessel receiving the irrigating fluid flowing out of the body cavity, and measuring means which detect the difference between the introduced quantity of irrigating fluid and the flowing-out quantity of irrigating fluid. The invention excels itself by the aspect that an electronic evaluation unit determines, on the basis of the output signal of the measuring means, the quantity of irrigating fluid lost and additionally the rate of variation of the lost quantity versus time.

12 Claims, 1 Drawing Sheet

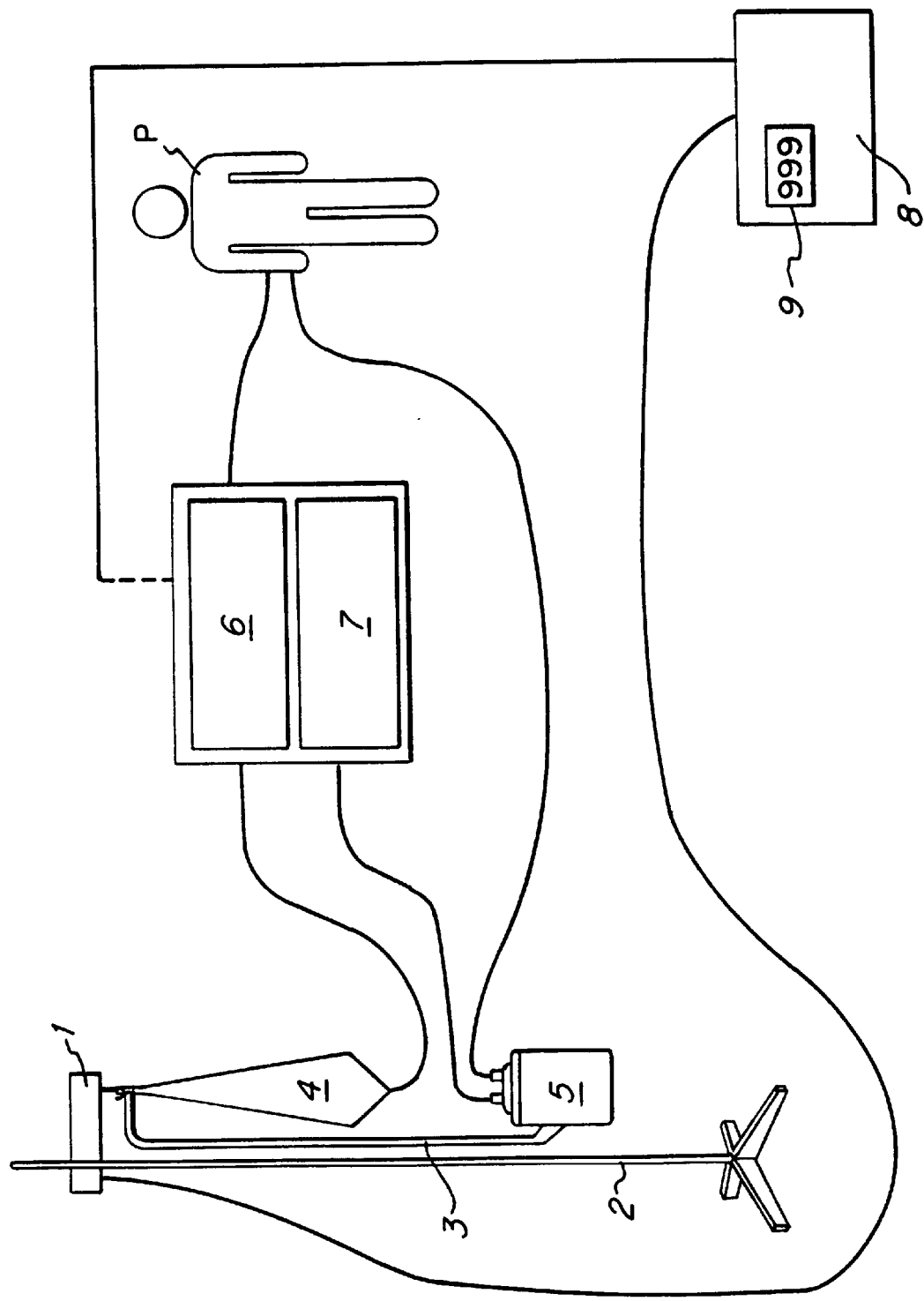

DEVICE FOR THE RINSING OF BODY CAVITIES

DESCRIPTION

1. Field of the Invention

The invention relates to an apparatus for irrigating body cavities with a fluid in accordance with the introductory clause of Patent claim 1.

Such apparatuses are manufactured and distributed, for instance, by Karl Storz GmbH & Co. by the brand name "Hamou Endomat" or "Uromat/Uropump" and are employed, inter alia, in the field of gynaecology and urology.

2. Prior Art

The fields of gynaecology and urology in particular involve a risk of intravasation (infiltration) when tissue is removed during the dilatation of a treated organ with an irrigating fluid. This operation is normally performed by means of a high-frequency loop, e.g. in the prostate gland or on the mucous membrane of the uterus.

It is therefore necessary to select the intra-uterine or intra-urethral pressure in a way that a sufficient dilatation and partly control of haemorrhage are achieved on the blood vessels by a certain overpressure. This overpressure on the blood vessels is usually termed "control" or "clamping".

If, however, major blood vessels are damaged by incision or section there is a risk of the irrigating fluid entering into the blood circulation. At flow rates of several 100 ml/min in "continuous flow" operation this may easily result in a dangerous infiltration of the irrigating liquid.

Such a situation had serious consequences for the patient's health. With a proper handling of the irrigating pumps employed today, which are provided with optimum pressure and flow control means, this risk may be reduced to a minimum. And yet the operators or the physician performing this operation must additionally still monitor and optimise the pressure and flow control functions during the operation. This means that the operating physician cannot perform the operation with unrestricted concentration. Moreover, it were helpful for less skilled and experienced physicians to obtain additional information for a further reduction of the risk of intravasation.

The company of Olympus Winter & Ibe offers at present an irrigating pump of the claimed general type which indicates the volumetric difference between the consumed volume of the irrigating solution and the aspirated volume of the irrigating solution. In that system the aspirated volume is determined by gravimetric means whilst the volume of consumed irrigating solution is determined by the number of revolutions of the irrigating pump.

This equipment entails the disadvantage that the differential volume furnishes only a definitely incomplete information about the occurrence of intravasation. In this respect the fact must be duly considered in particular that, depending on the surgeon's experience, a more or less substantial amount of irrigating liquid is lost through leaks or as a result of withdrawal of the endoscope or resectoscope, for instance, e.g. for cleansing purposes.

In engineering terms there were the possibility available to counter or collect these additionally lost quantities by a second collector vessel which is located, for instance, underneath the patient. In such a system a weighing cell ought to detect the additional losses. The output signal of this weighing cell could then correct the established differential volume insofar as only the irrigating liquid which entered the body is indicated. This possibility involves, however, the disadvantage of a more difficult handling by the user. Apart therefrom, this approach involves the risk of a certain liquid volume not being detected due to unskilled or improper handling of the instruments, e.g. the liquid volume flowing out between the body and the instrument. Moreover, lack of diligence in handling the collector vessel disposed underneath the patient, with resulting loading or unloading, may lead to the indication of an unduly small volumetric loss.

The laid-open German Patent Application DE 44 17 189 A1 of the prior German Patent Application P 44 17 189.7, which was published after the filing date of this application, discloses an apparatus for perfusion and aspiration of an (irrigating) liquid into and out of body cavities, wherein the volumetric flows are detected and the difference formed therefrom is displayed. This approach involves the disadvantage that only instantaneous values are permanently indicated so that the surgeon is not informed about the "total balance" of the irrigating liquid supplied and removed again.

BRIEF DESCRIPTION OF THE INVENTION

The present invention is now based on the problem of defining an apparatus which is easy to handle and which allows for optimum and reliable monitoring for intravasation even by less experienced physicians by providing the physician continuously about the total volume of irrigating fluid so far lost as well as about the instantaneous situation.

One inventive solution to this problem is defined in claim 1. Improvements of the invention are the subject matters of claims 2 et seq.

The present invention starts out from an apparatus for irrigating body cavities with a fluid, which comprises a reservoir for an irrigating fluid, a pumping unit pumping the irrigating fluid from the reservoir via an instrument through the body cavity to be treated, a collector vessel for collecting the irrigating fluid flow out of the body cavity, and measuring means which detect the difference between the introduced quantity of irrigating fluid and the flowing-off or aspirated quantity of irrigating fluid.

In accordance with the present invention the apparatus includes an electronic evaluation unit which determines, on the basis of the output signal from the measuring means, the quantity of lost irrigating fluid and additionally the rate of variation of the lost quantity versus time. Hence the problem arising in prior art as discussed above is solved by the invention by the provision that in an apparatus of the claimed general type the volumetric difference between the irrigating fluid consumed and the irrigating fluid aspirated is determined and indicated, in particular, and that additionally the rate of variation of this differential volume is determined and optionally displayed, for instance (cf. also claims 11 and 12.

Attention should be drawn explicitly to the aspect that the difference between the supplied and flowing-off quantities of fluid cannot be negative only but may also be positive due to additionally aspirated body fluids such as blood.

The pumping unit according to claim 2 expediently aspirates the irrigating fluid additionally from the body cavity. This provision ensures a better defined (return) flow of the irrigating fluid.

In accordance with claim 3 the pumping unit may include two pumps which allow for controlling or adjusting the flow-rates of the irrigating fluid to be introduced and the irrigating fluid aspirated individually (claim 10).

On principle, the measuring means may be configured in the most different ways and can detect the most different magnitudes as long as these only allow for a detection of the quantity of lost irrigating fluid.

Claim 4 defines a particularly expedient improvement wherein the measuring means determine the weight of the reservoir and the collector vessel. This configuration allows only for a simple and compact structure of the measuring means in particular but also for a precise detection of the individual measurands.

In accordance with claim 5 it is particularly preferred that the measuring means include only a single weighing cell which is loaded with both the weight of the reservoir and the weight of the collector vessel. This configuration does not only allow for a simple structure of the inventive apparatus but also increases the measuring accuracy because only a variation from a value must be detected which may be tared. With this design it is expedient, according to claim 6, to suspend the reservoir and the collector vessel on the weighing cell, hence reducing the required space even further.

It is, of course, also possible to provide two balances as measuring means.

In accordance with claim 7 an additional alert signal is expediently triggered in the form of an acoustic and/or optical alarm when a defined value, e.g. a determined rate of volumetric loss versus time, is exceeded. Such an alert signal may be triggered, for instance, when a flow of irrigating liquid has been detected which fully enters the patient's blood circulation or which corresponds to a flow which ends up outside the system e.g. during the cleaning of a resectoscope. In the event of an alarm the user or the surgeon must only decide whether a rapidly increasing differential volume signifies intravasation or merely represents a liquid loss due to handling.

As the critical rate of the (negative or positive) variation of the weight of the collector vessel or the reservoir is also dependent on the selected operation technique the user has the option to set the rate of variation at which an alarm is triggered according to claim 8.

The evaluating unit provided in accordance with the present invention is suitable for application not only for representing the measured values on a display unit for the physician but also for control of the pumping unit (claim 9).

In accordance with claim 10 it is possible in particular that the evaluating unit controls the pumping unit on the basis of the output signal of the measuring means in such a way that the flow of the irrigating fluid from the reservoir and the flow of the irrigating fluid into the collector vessel are approximately equal.

BRIEF DESCRIPTION OF THE DRAWING

In the following, the invention will be explained in more details with reference to an embodiment, referring to the drawing in which the only FIGURE is a schematic view of an inventive apparatus.

DESCRIPTION OF AN EMBODIMENT

The inventive apparatus for irrigating a body cavity of a patient P with a fluid comprises a weighing cell 1 which is fastened on a stand 2. A bar 3 is mounted on the weighing cell 1 for suspension of a reservoir 4 containing the irrigating fluid and of a collector vessel 5 receiving the irrigating fluid flowing out of the body cavity. The weighing cell 1 hence detects the total weight of the vessels 4 and 5.

The reservoir 4 is connected to an irrigating pump 6 of a pumping unit via a hose line, which pumping unit pumps the irrigating fluid from the reservoir 4 via an instrument (which is not illustrated) into the cavity of the body P to be treated.

Moreover, the pumping unit includes an aspirator pump 7 which aspirates the irrigating fluid through a hose line from the body cavity into the collector vessel 5.

The weighing cell 1 detects continuously the total weight of the two vessels 4 and 5. The output signal of the weighing cell 1 is applied to an electronic evaluation unit 8 via a line. The evaluation unit 8 detects the difference between the introduced quantity of irrigating fluid and the flowing-off amount of irrigating fluid on the basis of the output signal representing the total weight, and derives therefrom the quantity of irrigating fluid lost and additionally the rate of variation of the lost quantity versus time. The values so determined may be represented on a display unit 9 either by alternation or at the same time. Additional means are provided for an optical and/or acoustic alarm which is triggered when a defined rate of variation of the lost quantity is triggered.

Additional provisions may be made for causing the evaluation unit 8 to control the pumps 6 and 7 on the basis of the output signal of the weighing cell 1 in a way that the flow of the irrigating liquid from the reservoir 4 and the flow of the irrigating fluid into the collector vessel 5 are approximately equal.

We claim:

1. Apparatus for irrigating body cavities with a fluid, comprising a reservoir containing the fluid, a pumping unit which pumps the fluid from said reservoir into the body cavity to be treated, a collector vessel receiving the fluid flowing out of the body cavity, measuring means which generates a signal indicative of a difference between a quantity of fluid pumped into the body cavity and a quantity of fluid flowing out of the body cavity, and an electronic evaluation unit responsive to the measuring means signal to determine a rate of variation of lost fluid versus time.

2. Apparatus according to claim 1, characterized in that said pumping unit also aspirates the fluid from the body cavity.

3. Apparatus according to claim 2, characterized in that said pumping unit includes two pumps whereof one pumps the irrigating the fluid from said reservoir into the body cavity to be treated, whilst the other one aspirates fluid from the body cavity.

4. Apparatus according to claim 1, characterized in that said measuring means detects a weight of said reservoir and of said collector vessel.

5. Apparatus according to claim 4, characterized in that said measuring means include a single weighing cell loaded with both said reservoir and said collector vessel.

6. Apparatus according to claim 5, characterized in that said reservoir and said collector vessel are suspended on said weighing cell.

7. Apparatus according to claim 1, characterized in that said evaluation unit triggers an alarm when a defined rate of variation of the lost fluid is exceeded.

8. Apparatus according to claim 7, characterized in that the rate of variation at which an alarm is triggered may be set by the user.

9. Apparatus according to claim 1, characterized in that said evaluation unit controls said pumping unit.

10. Apparatus according to claim 9, characterized in that said evaluation unit controls said pumping unit on the basis of the measuring means signal in a way that the flow of the irrigating fluid from the reservoir and the flow of the irrigating fluid into said collector vessel are approximately equal.

11. Apparatus according to claim 1, characterized in that said evaluation unit displays the quantity of lost fluid and additionally the rate of variation of the lost fluid versus time.

12. Apparatus according to claim 11, characterized in that said display unit may be switched over from indicating the quantity of lost fluid to indicating the rate of variation of the lost fluid versus time.

* * * * *